United States Patent [19]
Nita et al.

[11] Patent Number: 5,368,557
[45] Date of Patent: * Nov. 29, 1994

[54] ULTRASONIC ABLATION CATHETER DEVICE HAVING MULTIPLE ULTRASOUND TRANSMISSION MEMBERS

[75] Inventors: Henry Nita, Mission Viejo; Timothy C. Mills, Newport Beach, both of Calif.

[73] Assignee: Baxter International Inc., Deerfield, Ill.

[*] Notice: The portion of the term of this patent subsequent to Dec. 7, 2010 has been disclaimed.

[21] Appl. No.: 61,872

[22] Filed: May 5, 1993

Related U.S. Application Data

[63] Continuation-in-part of Ser. No. 640,190, Jan. 11, 1991, Pat. No. 5,304,115.

[51] Int. Cl.$^5$ ............................................. A61B 17/70
[52] U.S. Cl. ........................................ 604/22; 601/2; 604/52
[58] Field of Search ............ 128/24 AA, 898; 604/21, 604/22, 49, 52; 606/159, 167, 169–171; 601/2

[56] References Cited

U.S. PATENT DOCUMENTS

| | | | |
|---|---|---|---|
| 3,352,303 | 11/1967 | Delaney | 128/24 AA |
| 3,433,226 | 3/1969 | Boyd . | |
| 3,526,219 | 9/1970 | Balamuth . | |
| 3,565,062 | 2/1971 | Kuris . | |
| 3,589,363 | 6/1971 | Banko . | |

(List continued on next page.)

FOREIGN PATENT DOCUMENTS

| | | |
|---|---|---|
| 189329 | 7/1986 | European Pat. Off. . |
| 234951 | 2/1987 | European Pat. Off. . |
| 293472 | 12/1988 | European Pat. Off. . |
| 315290 | 5/1989 | European Pat. Off. . |
| 347098 | 12/1989 | European Pat. Off. . |
| 208175 | 4/1990 | European Pat. Off. . |
| 443256 | 8/1991 | European Pat. Off. . |
| 472368 | 2/1992 | European Pat. Off. . |
| 2424733 | 1/1980 | France . |
| 2641693 | 7/1990 | France . |
| 2349120 | 4/1975 | Germany . |
| 2453058 | 5/1976 | Germany . |
| 2453126 | 5/1976 | Germany . |
| 2541919 | 3/1977 | Germany . |
| 2703486 | 12/1977 | Germany . |
| 3706921 | 9/1987 | Germany . |
| 3707567 | 9/1987 | Germany . |
| 3826414 | 2/1989 | Germany . |
| 3812836 | 4/1990 | Germany . |
| 2208138 | 3/1989 | United Kingdom . |
| 2212267 | 7/1989 | United Kingdom . |
| WO87/01276 | 3/1987 | WIPO . |
| WO87/05793 | 10/1987 | WIPO . |
| WO89/05123 | 7/1989 | WIPO . |
| WO89/06515 | 7/1989 | WIPO . |
| WO89/07419 | 8/1989 | WIPO . |
| WO90/01300 | 2/1990 | WIPO . |
| WO90/07383 | 7/1990 | WIPO . |
| WO91/02489 | 3/1991 | WIPO . |
| WO91/14401 | 10/1991 | WIPO . |

OTHER PUBLICATIONS

Circulation, vol. 81, No. 2,2/190, "Application of a New Phased-Arrayed Ultrasound Imaging Catheter in the Assessment of Vascular Dimensions", pp. 660–666.
2643272, Aug. 24, 1990, Abstract.
GM8119209, Sep. 1981, Abstract.

1531659, Jul. 21, 1977, Abstract.

Primary Examiner—C. Fred Rosenbaum
Assistant Examiner—Michael Rafa
Attorney, Agent, or Firm—Stetina & Brunda

[57] ABSTRACT

An ultrasound catheter device for transmitting ultrasound into a mammalian body comprising an elongate catheter body having at least one lumen extending longitudinally therethrough. Also extending longitudinally through the lumen are at least two ultrasound transmission members, each of which have a proximal end coupleable to an external ultrasound source and a distal end which terminates near the distal end of the catheter.

24 Claims, 3 Drawing Sheets

U.S. PATENT DOCUMENTS

| | | |
|---|---|---|
| 3,618,594 | 11/1971 | Banko . |
| 3,823,717 | 7/1974 | Pohlman et al. . |
| 3,861,391 | 1/1975 | Antonevich et al. . |
| 3,896,811 | 6/1975 | Storz . |
| 4,188,952 | 2/1980 | Loschilov et al. . |
| 4,214,586 | 7/1980 | Mericle et al. . |
| 4,223,676 | 9/1980 | Wuchinich et al. . |
| 4,366,819 | 1/1983 | Kaster . |
| 4,431,006 | 2/1984 | Trimmer et al. . |
| 4,587,958 | 5/1986 | Noguchi et al. . |
| 4,587,972 | 5/1986 | Morantte, Jr. . |
| 4,589,419 | 5/1986 | Laughlin et al. . |
| 4,665,906 | 5/1987 | Jervis . |
| 4,692,139 | 9/1987 | Stiles . |
| 4,750,902 | 6/1988 | Wuchinich et al. . |
| 4,794,931 | 1/1989 | Yock . |
| 4,799,496 | 1/1989 | Hargreaves et al. . |
| 4,800,876 | 1/1989 | Fox et al. . |
| 4,808,153 | 2/1989 | Parisi . |
| 4,821,731 | 4/1989 | Martinelli et al. . |
| 4,841,977 | 6/1989 | Griffith et al. . |
| 4,844,092 | 7/1989 | Rydell et al. . |
| 4,867,141 | 9/1989 | Nakoda et al. ................ 604/22 |
| 4,870,953 | 10/1989 | Don Micheal et al. . |
| 4,898,565 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,924,863 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden et al. . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,267,954 | 12/1993 | Nita ................ 604/22 |

ULTRASONIC ABLATION CATHETER DEVICE HAVING MULTIPLE ULTRASOUND TRANSMISSION MEMBERS

RELATED APPLICATION

This patent application is a continuation-in-part of U.S. patent application Ser. No. 07/640,190 filed Jan. 11, 1991 entitled ULTRASOUND ANGIOPLASTY DEVICE INCORPORATING IMPROVED TRANSMISSION MEMBER AND ABLATION PROBE, U.S. Pat. No. 5,304,115 the entire disclosure of such prior patent application being hereby expressly incorporated herein by reference.

FIELD OF THE INVENTION

The present invention relates generally to medical devices and methodology, and more particularly to devices and methodology for removing unwanted matter from tubular anatomical structures such as blood vessels.

BACKGROUND OF THE INVENTION

Ultrasonic energy has been established as a viable means of removing obstructive matter (e.g., atherosclerotic plaque or thromboembolic material) from blood vessels. Examples of ultrasonic devices purportedly useable to remove or ablate vascular obstructions are found in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,935 (Don-Michael, et al.), 5,069,664 (Suess, et al.) and 4,920,954 (Alliger, et al.), as well as other patent applications WO 87-05739 (Cooper), WO 89-06515 (Bernstein, et al.), WO 90-0130 (Sonic Needle Corp.), EP 316,789 (Don-Michael, et al.), DE 3,821,836 (Schubert), DE 2,438,648 (Pohlman) and EP 0443256 A1 (Baruch).

U.S. patent application Ser. No. 07/640,190 entitled ULTRASONIC ANGIOPLASTY DEVICE INCORPORATING IMPROVED TRANSMISSION MEMBER AND ABLATION PROBE, of which this application is a continuation-in-part, describes an ultrasound catheter device comprising a flexible tubular catheter having a wire-like elongate ultrasound transmission member which extends longitudinally through the catheter. Ultrasonic energy may be passed through the ultrasound transmission member to effect ultrasonic ablation or destruction of unwanted material located adjacent the distal end of the catheter.

Although the disclosure of U.S. patent application Ser. No. 07/640,190 includes certain configurational and/or material modifications intended to improve the flexibility or bendability of the ultrasound transmission member, there remains a need in the art for further improvements whereby the flexibility or bendability of an ultrasound catheter may be optimized while maintaining the requisite efficiency of energy transmission through the length of the catheter.

SUMMARY OF THE INVENTION

The present invention provides an improved ultrasonic catheter device for effecting ultrasonic ablation of unwanted matter within an anatomical passageway, pathway, cavity, blood vessel or organ of a mammalian body. The ultrasonic catheter of the present invention comprises a flexible catheter body having two or more ultrasound transmission members extending longitudinally therethrough. Each of the two or more ultrasound transmission members may be of relatively small cross-sectional dimension (e.g., 1 mm–1.0 mm in diameter). Each ultrasound transmission member may be coupled to or contacted to the distal end of the catheter and/or a distal "head" member positioned at the distal end of the catheter. As such, ultrasonic energy passing through the individual ultrasound transmission members will result in ultrasonic vibration of the distal portion of the catheter and/or the distal "head" member.

Further in accordance with the invention, there is provided an improvement to any ultrasound catheter of the prior art and comprising a flexible catheter body having an ultrasound transmission member, such as a wire, extending longitudinally therethrough, said improvement comprising the provision of two or more separate ultrasound transmission members (e.g., wires) for transmitting said ultrasound energy longitudinally through at least a portion of said catheter body and, associated means for causing the separate quanta of ultrasound energy transmitted through said two or more ultrasound transmission members to combine or joint at a treatment sight at or adjacent the distal end of the catheter.

BRIEF DESCRIPTION OF THE DRAWINGS

FIG. 3 is a longitudinal sectional view through line 3—3 of FIG. 2.

DETAILED DESCRIPTION OF THE PREFERRED EMBODIMENT

The following detailed description and the accompanying drawings are provided for purposes of describing and illustrating a presently preferred embodiment of the invention only. The following detailed description and the accompanying drawings are not intended to in any way limit the scope of the invention, as defined in the accompanying claims and the equivalents thereof.

Figure 1:
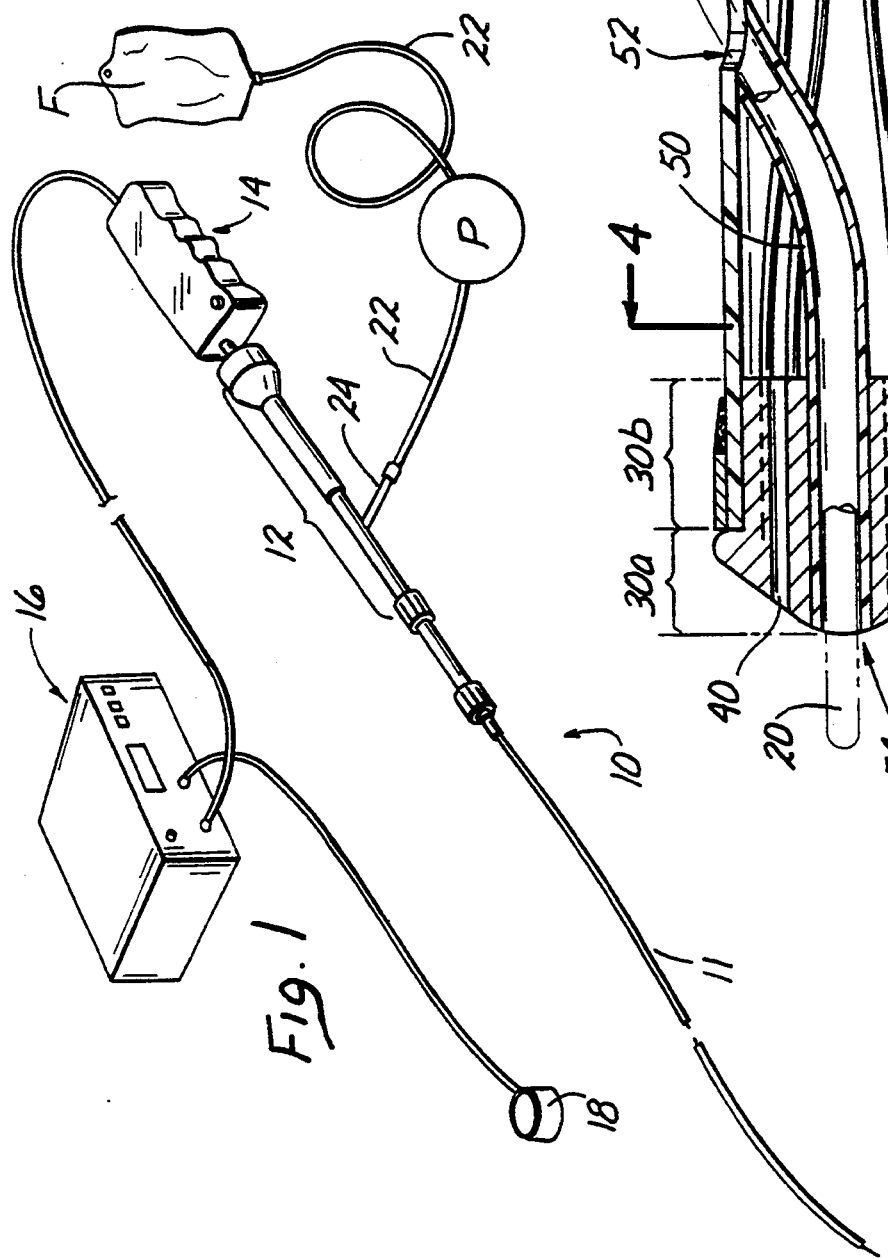
FIG. 1 is a perspective view of an ultrasound catheter of the present invention operatively connected to an ultrasound generating system.

Referring to the drawings, FIG. 1 shows an ultrasound catheter device 10 of the present invention comprising an elongate flexible catheter portion 11 and a proximal end connector assembly 12. The ultrasound catheter device 10 is operatively coupled, by way of proximal connector assembly 12, to ultrasound transducer 14. (Model UAT-1000, Baxter Healthcare Corporation, Edwards Less Invasive Surgery Division, 17221 Redhill Avenue, Irvine, Calif. 92714). The ultrasound transducer 14 is connected to a signal generator 16 (Model UAG-1110, Baxter Healthcare Corporation, Edwards Less Invasive Surgery Division, 17221 Redhill Avenue, Irvine, Calif. 92714). The signal generator 16 is provided with a foot actuated on-off switch 18. When the foot actuated on-off switch 18 is depressed, the signal generator 16 sends an electrical signal to the ultrasound transducer 14. The ultrasound transducer 14 then converts the electrical signal to ultrasonic energy. Such ultrasonic energy subsequently passes through the ultrasound catheter device 10 of the present invention, being thereby delivered to the distal end of the device 10.

A guidewire 20 may be utilized in conjunction with the catheter device 10, as more fully described herebelow.

Also, in the embodiment shown, a source of coolant fluid F, (e.g., 0.9% NaCl solution) is connected, by way of an infusion tube 22, to an infusion port or sidearm 24 of the proximal end connector assembly 12. Coolant fluid F may thereby be infused into and/or through the catheter device 10. Such flow of coolant fluid may be utilized to prevent overheating of the ultrasound transmission components housed with the ultrasound catheter device 10 of the invention.

Figure 2:
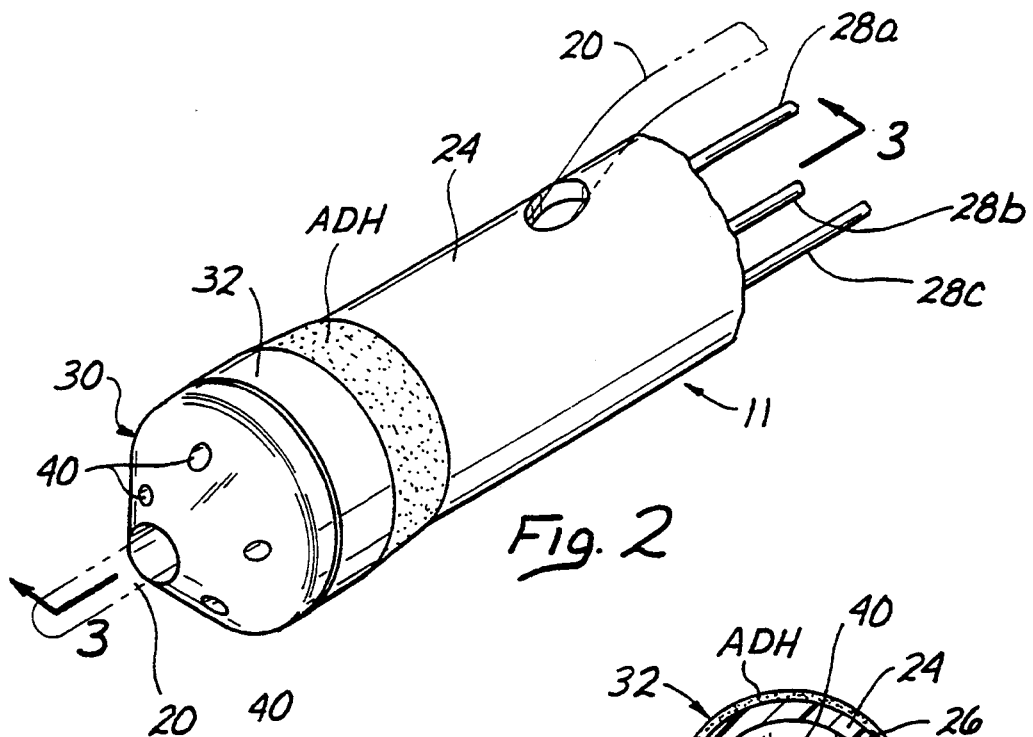
FIG. 2 is an enlarged perspective view of the distal end of an ultrasound catheter of the present invention.
Figure 4:
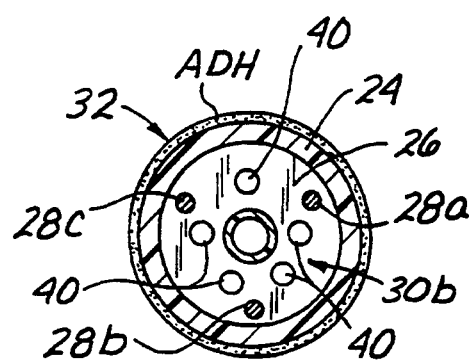
FIG. 4 is a cross-sectional view through line 4—4 of FIG. 3.

The distal aspect of the catheter portion 11 of the device 10 of the present invention is shown, in detail, in FIGS. 2, 3 and 4. As shown, the elongate catheter portion 11 of the device 10 comprises a flexible catheter body 24 preferably formed of flexible plastic material such as nylon (e.g., Pebax TM, Atochimie, Cour be Voie, Hauts-Ve-Sine, France.) The flexible catheter body 24 is preferably in the form of an elongate tube having one or more lumens extending longitudinally therethrough. In the embodiment shown, a single lumen 26 extends longitudinally through the tubular catheter body 24. Three(3) ultrasound transmission members 28a, 28b, 28c extend longitudinally through the lumen 26 of the catheter body 24. Such three(3) ultrasound transmission members 28a, 28b, 28c serve to transmit ultrasonic energy from the proximal end connector apparatus 12 to the distal head 30 mounted on the distal end of the device 10.

The distal head 30 comprises a substantially rigid member affixed to the distal end of the catheter body 24. In the embodiment shown, the distal head 30 comprises a generally frustoconical distal portion 30a, and a generally cylindrical proximal portion 30b. The proximal portion 30b of distal head member 30 is inserted into the open distal end of the tubular catheter body 24, as shown. An annular ring member 32 is positioned about the distal end of the catheter body 24 so as to exert inward pressure on the catheter body, thereby gripping and holding the proximal portion 30b of the distal head 30 within the distal end of the lumen 26 of catheter body 24. A quantity of adhesive ADH is applied about the proximal edge of annular ring member 32 so as to affix the annular ring member 32 in position on the distal end of the catheter body 24, as shown. Such adhesive may be gently angled or tapered so as to form a gradual inward slope from the outer surface of the annular ring member 32 to the outer surface of the catheter body 24. Preferably, the outer diameter of the annular ring member 32 is approximately the same as the outer diameter of the distal portion 30a of the distal head member 30, thereby forming a generally smooth outer surface at the juncture of the distal head member 30 and the catheter body 24, as shown.

In the particular embodiment shown in the figures, the three(3) ultrasound transmission members 28a, 28b and 28c are individually inserted into bores 34 which extend longitudinally into the proximal portion of the distal head member 30. The distal ends of the individual ultrasound transmission meanders 28a, 28b and 28c are then firmly held within bores 34 by frictional engagement of each member 28a, 28b and 28c to the surrounding material of the distal head 30, or by other mechanical or chemical affixation means such as weldments, adhesive, etc. Firm affixation of the individual ultrasound transmission members 28a, 28b and 28c to the distal head 30 serves to facilitate direct transmission of the quanta of ultrasonic energy passing through the individual ultrasound transmission members 28a, 28b and 28c to the distal head member 30. As a result, the distal head member 30, and a distal portion of the tubular catheter body 24, are caused to undergo ultrasonic vibration in accordance with the combined quanta of ultrasonic energy being transmitted through the separate ultrasound transmission members 28a, 28b and 28c.

Fluid outflow apertures 40 extend longitudinally through distal head member 30 so as to permit the coolant fluid F to flow from the lumen 26 out of the distal end of the device 10. Such flow of fluid through lumen 26 serves to bathe the outer surfaces of the individual ultrasound transmission members 28a, 28b and 28c, thereby providing for an equilibration of temperature between the coolant fluid F and the matter of the individual ultrasound transmission members 28a, 28b and 28c. Thus, the temperature and/or flow rate of coolant fluid F may be adjusted to provide adequate cooling and/or other temperature control of the individual ultrasound transmission members 28a, 28b, 28c.

A tubular guidewire lumen or passageway 50 extends through the distal portion of the catheter body 24. The guidewire lumen 50 comprises a tube having a diameter of approximately 0.1-1,0 mm. A sidewall guidewire passage port 52 is formed in the sidewall of the catheter body 24 approximately 0.1-40 cm from the distal end of the catheter 11. A distal guidewire passage port 54 extends longitudinally through distal head member 30. The guidewire lumen or passageway 50 comprises a dedicated tube extending between the sidewall guidewire passage port 52 and distal guidewire passage port 54. A guidewire 20 may be inserted into the distal guidewire passage port 54, advanced through the guidewire lumen or passageway 50 and allowed emerge from guidewire sidewall passage font 52, as shown in FIG. 3. The device 10 may, thus, be advanced and/or retracted over a pre-positioned guidewire in accordance with typical operative technique utilized in interventional cardiology procedures such as percutaneous transluminal angioplasty procedures.

Figure 5:
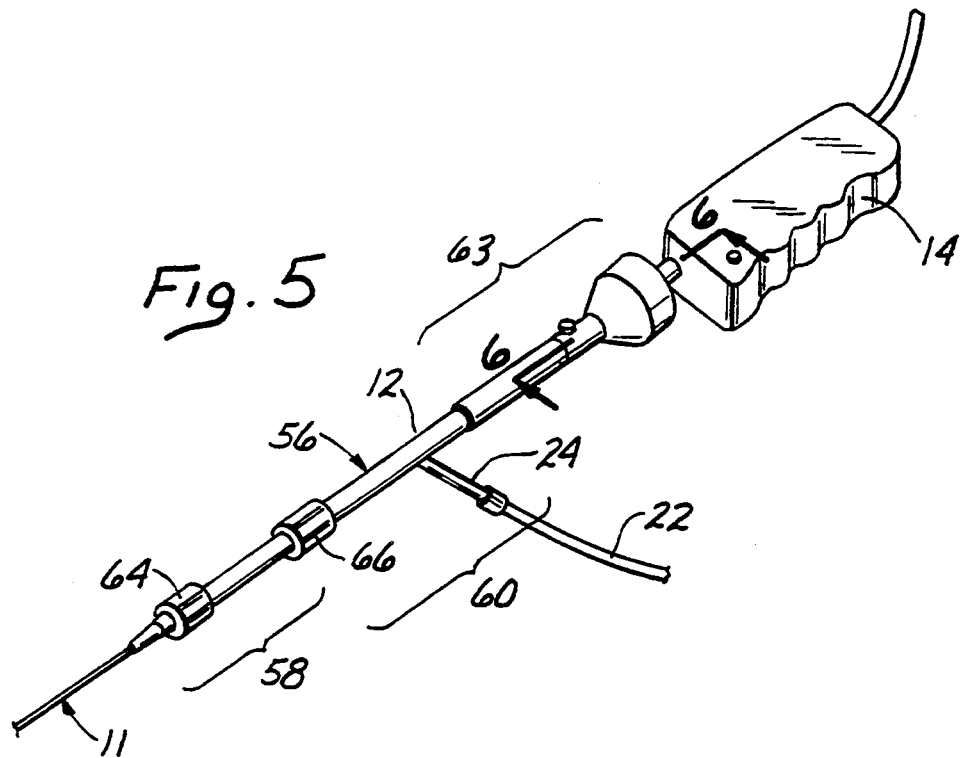
FIG. 5 is a perspective view of one embodiment of a proximal connector apparatus whereby the ultrasound catheter of the present invention is operatively coupled to an ultrasound transducer.
Figure 6:
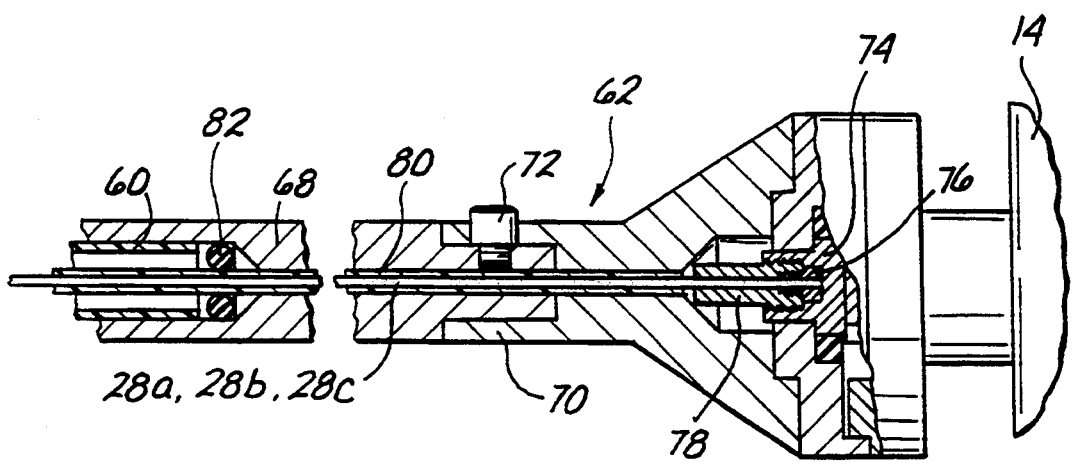
FIG. 6 is a partial longitudinal sectional view through line 6—6 of FIG. 5.

The proximal connector assembly 12 of the device 10 is shown, in detail, in FIGS. 5 and 6. The proximal connector assembly 12 comprises an elongate, rigid body 56 defining a frontal portion 58, a mid-portion 60 and a rear portion 62. The frontal portion 58 of the elongate body 56 is firmly connected to the proximal end of the catheter portion 11 by way of a threaded gripping member 64 engaged thereto. In this respect, the proximal end of the catheter portion 11 preferably has a flared configuration and includes an annular flange formed on the outermost end thereof which is brought into sealed engagement with the connector assembly 12 when the gripping member 64 is threadably engaged to the body 56. The proximal end of the frontal portion 58 is connected to the distal end of the mid-portion 60 of the elongate body 56 by way of a second gripping member 66. As will be recognized, to facilitate the aforementioned construction, threads are formed on the distal ends of the frontal portion 58 and the mid-portion 60. Additionally, as seen in FIG. 6, the proximal end of the mid-portion 60 is non-threaded and is slideably received into a corresponding bore formed in the distal end of the rear portion 62 of the body 56. In this respect, the mid-portion 60 is maintained in engagements to the rear portion 62 via the utilization of an adhesive or other suitable affixation method.

Referring now to FIG. 6, the rear portion 62 of the body 56 comprises a distal member 68, the distal end of which is adapted to receive the proximal end of the mid-portion 60, and a generally frusto-conical proximal member 70. The proximal end of the distal member 68 is formed of a reduced diameter and is slideably inserted into a complimentary recess defined in the distal end of the proximal member 70. The proximal member 70 is maintained in engagement to the distal member 68 via the utilization of a threaded fastener 72 such as a screw which is extended through the bore defining wall of the proximal member 70 and into a threaded aperture disposed within the reduced diameter proximal end of the distal member 68. The ultrasound transmission members 28a, 28b, 28c extend longitudinally through the entire catheter portion 11 and through the proximal end of the connector assembly 12. The ultrasound transmission members 28a, 28b, 28c are then inserted into and engaged by a threaded proximal connector 74 which is positioned within a cylindrical recess formed in the proximal end of the proximal member 70. The ultrasound transducer 14 is cooperatively engaged to the proximal connector 74 in a manner adapted to accomplish the passage of ultrasonic energy through the ultrasound transmission members 28a, 28b, 28c in a distal direction to the distal end of the catheter body 24.

The extreme proximal end of the proximal member 70 is provided with a sonic connector assembly or apparatus configured to effect operative attachment of the proximal ends of the ultrasound transmission members 28a, 28b, 28c to the horn of the ultrasound transducer 14. The sonic connector assembly or apparatus is preferably configured and constructed to permit passage of ultrasound energy through the ultrasound transmission members 28a, 28b, 28c with minimal lateral side-to-side movement of the ultrasound transmission members 28a, 28b, 28c while, at the same time, permitting unrestricted longitudinal forward/backward vibration or movement of the ultrasound transmission members 28a, 28b, 28c. Specifically, a distal portion of the body of the threaded proximal connector 74 is configured to receive therein a compressible gripping ferrule 76. The compressible gripping ferrule 76 has a small central aperture formed therethrough through which the ultrasound transmission members 28a, 28b, 28c pass, as shown. A frontal member 78 is threadably tightened within the frontal portion of the body of the proximal connector 74 so as to compress the gripping ferrule 76, thereby causing the gripping ferrule 76 to firmly grip and hold the ultrasound transmission members 28a, 28b, 28c in place within the body of the proximal connector 74. The proximal connector 74 may then be compressed or crimped inwardly so as to be additionally crimp connected or crimp fit to the proximal ends of the ultrasound transmission members 28a, 28b 28c, thereby providing further gripping and attachment of the sonic connector assembly to the proximal ends of the ultrasound transmission members 28a, 28b, 28c. The proximal connector 74 is further formed to permit the distal end of the ultrasound transducer horn to be releasably engaged thereto and thus releasably attached to the sonic connector assembly. Thus, the frontal member 78, gripping ferrule 76, and proximal connector 74 combine to form a sonic connector assembly to which the horn of the ultrasound transducer 14 may be attached and through which the ultrasonic energy may be transmitted into the ultrasound transmission members 28a, 28b, 28c. A lumen 80 extending through the rear and mid-portions 62, 60 of the connector assembly 12 is specifically sized to be large enough to permit the ultrasound transmission members 28a, 28b, 28c to pass therethrough with a small amount of space remaining between the outer surfaces of the ultrasound transmission members 28a, 28b, 28c and the innerlumenal surface of the lumen 80. Also disposed within the mid-portion receiving bore formed in the distal end of the distal member 68 is on 0-ring 82 which is used to prevent the passage of any fluid along the outer surfaces of the lumen 80 into the proximal member 70 of the rear portion 62.

Figure 7A:
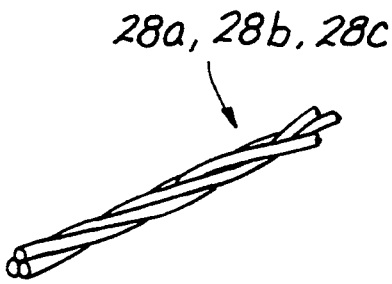
FIG. 7a is a partial perspective view of multiple ultrasound transmission members of an ultrasound catheter of the present invention wherein said multiple ultrasound transmission members are longitudinally wound about one another.
Figure 7B:
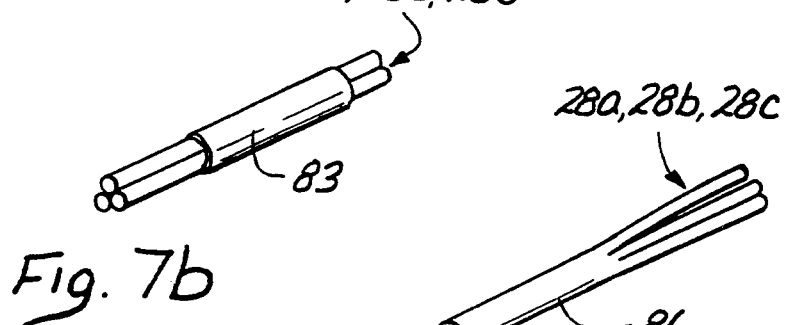
FIG. 7b is a partial perspective view of multiple ultrasound transmission members of an ultrasound catheter device of the present invention wherein said multiple ultrasound transmission members are at least partially surrounded by an external sleeve member.
Figure 7C:
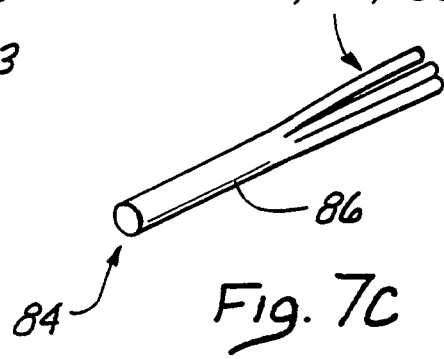
FIG. 7c is a partial perspective view of a furcated ultrasound transmission member of an ultrasound catheter device of the present invention.

Referring now to FIGS. 7a, 7b, 7c, though the distal ends of the ultrasound transmission members 28a, 28b, 28c are attached to the distal head 30 in spaced relation, the proximal portions of the ultrasound transmission members 28a, 28b, 28c extending through the lumen 80 must be configured to facilitate the passage therethrough and/or to otherwise form a substantially unitary proximal end portion coupleable to an external ultrasound source such as ultrasound transducer 14. In this respect, as seen in FIG. 7a, the proximal portions of the ultrasound transmission members 28a, 28b, 28c may be longitudinally wound about one another, thus forming a resultant structure which is sized to be passed through the lumen 80. Alternatively, as seen in FIG. 7b, the ultrasound transmission members 28a, 28b, 28c may be longitudinally abutted against each other and maintained in such orientation via an external sleeve member 83 surrounding the bundled ultrasound transmission members 28a, 28b, 28c. As will be recognized, the outer diameter of the sleeve member 83 is sized so that the same may be easily received into the lumen 80. Additionally, the ultrasound transmission members 28a, 28b, 28c may be surrounded by a single, elongate sleeve member 82 or by two or more sleeve members of shorter length. Further, as seen in FIG. 7c, the ultrasound transmission members 28a, 28b, 28c may be defined by a furcated transmission member 84 having a proximal portion 86 of unitary construction which is sized to be insertable through the lumen 80.

As previously explained, coolant fluid F may be circulated through the lumen 26 to bathe the outer surfaces of the ultrasound transmission members 28a, 28b, 28c, thereby providing a desired equilibration of temperature. In this respect, the temperature and flow rate of the coolant fluid F may be specifically controlled to maintain the temperature of the ultrasound transmission members 28a, 28b, 28c at a desired temperature within their optimal working range. In particular, in embodiments of the invention wherein the ultrasound transmission members 28a, 28b, 28c are formed of a metal alloy which exhibits optimal physical properties (e.g., superelasticity) within a specific range of temperatures, the temperature and flow rate of the coolant fluid F infused into the sidearm 24 may be specifically controlled to maintain the temperature of the ultrasound transmission members 28a, 28b, 28c within the range of temperatures at which they demonstrate the most desirable physical properties. For example, in embodiments of the invention wherein the ultrasound transmission members 28a, 28b, 28c are formed of a shape memory alloy which exhibits superelasticity when in its martensite state, but which loses superelasticity as it transitions to an austenite state, it will be desirable to adjust the temperature and flow rate of the coolant fluid F infused through the sidearm 24 so as to maintain the shape and memory alloy of the ultrasound transmission members 28a, 28b, 28c within a temperature range at which the alloy will remain in its martensite state and will not transition to an austenite state. The temperature at which such shape memory alloys transition from a martensite state to an austenite state is known as the "martensite transition temperature" (Ms) of the material. Thus, in these embodiments, the coolant fluid F infused through the sidearm 24 will be at such temperature, and will be infused at such rate, as to maintain the shape memory alloy of the ultrasound transmission members 28a, 28b, 28c below their martensite transition temperature (Ms).

As such, the ultrasound transmission members 28a, 28b, 28c are preferably formed of one or more materials which exhibit super-elasticity. Such materials should preferably exhibit super-elasticity consistently within the range of temperatures normally encountered by the ultrasound transmission members 28a, 28b, 28c during operation of the catheter device 10. Specifically, all or part of the ultrasound transmission members 28a, 28b, 28c may be formed of one or more metal alloys known as "shape memory alloys".

Examples of super-elastic metal alloys which are useable to form the ultrasound transmission members 28a, 28b, 28c of the present invention are described in detail in the U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission members 28a, 28b, 28c of the present invention operate, any and all of which super-elastic metal alloys may be useable to form the super-elastic ultrasound transmission members 28a, 28b, 28c.

In particular, one presently preferred super-elastic metal alloy of which the ultrasound transmission members 28a, 28b, 28c may be formed is a nickel-titanium alloy wire made up of 55.8 weight percent nickel/balance titanium (or 50.8 atomic percent nickel/balance titanium). Such material is commercially available as Tinel ™ wire from Raychem Corporation, Menlo Park, Calif.

The preferred nickel-titanium alloy containing 50.8 atomic percent nickel (i.e., 55.8 weight percent nickel/balance titanium) is one of a family of Ni-Ti alloys which are commercially available under the brand name Tinel ® from Raychem Corporation, Menlo Park, Calif. 94025. The physical properties of the preferred nickel-titanium alloy having 50.8% atomic percent nickel/balance titanium are as follows:

| Properties of NiTi Alloy Having 50.8 At. % Nickel/Balance Titanium | | |
|---|---|---|
| Property | Units | Value |
| Superelastic Temperature Range | °C. | 20 to 80 |
| Loading Plateau Stress (at 20° C.) | MPa | 480 |
| Unloading Plateau Stress | Mpa | 135 |
| Permanent Set (at 20° C. after 8% strain) | % | 0.2 |
| Ultimate Tensile Strength (at 20° C.) | Mpa | 1150 |
| | Ksi | 170 |
| Elongation at Failure | % | 10 |
| Melting Point | °C. | 1350 |
| Density | g/cm | 6.5 |
| | lbs/cu. Inch | 0.235 |

*Typical Values for Cold Worked and Shape Set Condition

As will be recognized, in any embodiment of the present invention, the ultrasound transmission members 28a, 28b, 28c may be tapered, narrowed, or otherwise reduced in cross-sectional dimension within the catheter device 10 so as to decrease the rigidity of the ultrasound transmission members 28a, 28b, 28c and/or to cause amplification of the ultrasound transmitted to and from the distal ends thereof.

Additional modifications and improvements of the present invention may also be apparent to those skilled in the art. Thus, the particular combination of parts described and illustrated herein is intended to represent only one embodiment of the present invention and is not intended to serve as limitations of alternative devices within the spirit and scope of the invention.

What is claimed is:

1. An ultrasound catheter device for transmitting ultrasound into a mammalian body, said device comprising:
   a) an elongate flexible catheter body having a proximal end, a distal end, and at least one lumen extending longitudinally therethrough;
   b) at least two ultrasound transmission members extending longitudinally through said at least one lumen, each of said ultrasound transmission members having a proximal end coupled to an external ultrasound source and a distal end which terminates near the distal end of said catheter;
   c) said at least two ultrasound transmission members being configured and constructed to simultaneously transmit ultrasound energy to the distal end of said catheter body; and
   d) a distal head member attached to the distal end of said catheter body and coupled to the distal ends of said at least two ultrasound transmission members such that said distal head member will vibrate in accordance with ultrasound being simultaneously transmitted through said at least two ultrasound transmission members.

2. The device of claim 1 wherein said distal head member comprises a plug member inserted into the distal end of said catheter body.

3. The device of claim 2 wherein said distal head member further comprises at least one fluid passage aperture extending longitudinally through said distal head member to permit fluid to flow out of the lumen of said catheter body through said distal head member.

4. The device of claim 1 wherein said distal head member further comprises a guidewire passage aperture extending longitudinally through said distal head member to permit passage of a guidewire therethrough.

5. The device of claim 4 further comprising:
a sidewall guidewire passage aperture formed in the sidewall of said catheter body; and
a tubular guidewire lumen member extending between said sidewall guidewire passage aperture formed in the sidewall of said catheter body and said guidewire passage aperture formed in said distal head;
said sidewall guidewire passage aperture, said tubular guidewire lumen and said distal head guidewire passage aperture thereby combining to form a guidewire passageway through which a guidewire may be passed.

6. The device of claim 1 wherein said at least two ultrasound transmission members comprise first, second and third ultrasound transmission members.

7. The device of claim 1 wherein said ultrasound transmission members are formed of superelastic metal alloy.

8. The device of claim 7 wherein said superelastic metal alloy is NiTi.

9. The device of claim 1 further comprising:
a guidewire passage lumen having a proximal end and a distal end, said guidewire passage lumen extending through at least a portion of said catheter body to permit a guidewire to be passed therethrough.

10. The device of claim 1 wherein said at least two ultrasound transmission members are combined at their proximal ends to form a substantially unitary proximal end portion to facilitate coupling or attachment of said proximal end portion to an ultrasound energy source.

11. The device of claim 10 wherein said at least two ultrasound transmission members are fused at their proximal ends to form said substantially unitary proximal end portion.

12. The device of claim 10 wherein the proximal ends of said at least two ultrasound transmission members are surrounded by a sleeve member to form said substantially unitary proximal end portion.

13. The device of claim 10 wherein the proximal ends of said at least two ultrasound transmission members are entertwined to form said substantially unitary proximal end portion.

14. The device of claim 7 wherein said superelastic metal alloy is selected from the group of metal alloys consisting of:
metal alloys formed by the combination of at least two metal elements, said metal elements being combined in relative amounts which result in said metal alloy having an ultimate tinsel strength at 20° C. of approximately 1150 Mpa and a super elastic temperature range of approximately 20°–80° C.

15. The device of claim 14 wherein said relative amounts of said metal elements are further such that said alloy exhibits an unloading plateau stress at 20° C. of approximately 135 Mpa.

16. The device of claim 14 wherein said relative amounts of said metal elements are further such that said alloy exhibits a permanent set at 20° C. after 8 percent strain of approximately 0.2 percent.

17. The device of claim 14 wherein said relative amounts of said metal elements are further such that said alloy exhibits an elongation at failure of approximately 10.0 percent.

18. The device of claim 14 wherein said relative amounts of said metal elements are further such that said alloy exhibits a melting point of approximately 1350° C.

19. The device of claim 14 wherein said relative amounts of said metal elements are further such that said alloy has a density of approximately 6.5 g/cm.

20. The device of claim 1 wherein sufficient space exists within said at least one lumen to permit a liquid to flow through said at least one lumen and around said at least two ultrasound transmission members to effect temperature control of said ultrasound transmission members; and wherein said device further comprises:
e) a liquid inlet opening formed into said at least one lumen near the proximal end of said catheter body; and
f) at least one liquid outlet opening formed into said at least one lumen near the distal end of said catheter body;
g) a temperature control liquid being thereby infusable into said inlet opening, through said lumen and out of said outlet opening(s) to effect temperature control of said at least one ultrasound transmission member during operation of said device.

21. An ultrasound catheter device for transmitting ultrasound into a mammalian body, said device comprising:
a) an elongate flexible catheter body having a proximal end, a distal end, and at least one lumen extending longitudinally therethrough;
b) at least two ultrasound transmission members extending longitudinally through said at least one lumen, each of said ultrasound transmission members having a proximal end coupled to an external ultrasound source and a distal end which terminates near the distal end of said catheter; and
c) said at least two ultrasound transmission members being configured and constructed to simultaneously transmit ultrasound energy to the distal end of said catheter body;
d) wherein said at least two ultrasound transmission members are combined at their proximal ends to form a substantially unitary proximal end portion to facilitate coupling or attachment of said proximal end portion to an ultrasound energy source.

22. The device of claim 21 wherein said at least two ultrasound transmission members are fused at their proximal ends to form said substantially unitary proximal end portion.

23. The device of claim 21 wherein the proximal ends of said at least two ultrasound transmission members are surrounded by a sleeve member to form said substantially unitary proximal end portion.

24. The device of claim 21 wherein the proximal ends of said at least two ultrasound transmission members are entertwined to form said substantially unitary proximal end portion.

* * * * *